(12) United States Patent
Daniel et al.

(10) Patent No.: US 11,504,240 B2
(45) Date of Patent: Nov. 22, 2022

(54) MODULAR BONE GRAFT CAGE

(71) Applicant: DEPUY SYNTHES PRODUCTS, INC., Raynham, MA (US)

(72) Inventors: Steffan Daniel, Zuchwil (CH); André Furrer, Zuchwil (CH); Scott Larsen, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 124 days.

(21) Appl. No.: 16/893,390

(22) Filed: Jun. 4, 2020

(65) Prior Publication Data
US 2021/0378828 A1    Dec. 9, 2021

(51) Int. Cl.
*A61F 2/28* (2006.01)
*A61F 2/30* (2006.01)

(52) U.S. Cl.
CPC .... *A61F 2/2846* (2013.01); *A61F 2002/2835* (2013.01); *A61F 2002/30131* (2013.01); *A61F 2002/30477* (2013.01)

(58) Field of Classification Search
CPC .... A61F 2002/2835; A61F 2002/30131; A61F 2002/30153; A61F 2002/30383; A61F 2002/30784; A61F 2230/0013; A61F 2002/30261; A61F 2/2846
See application file for complete search history.

(56) References Cited

U.S. PATENT DOCUMENTS

| | | | |
|---|---|---|---|
| 3,710,789 A | 1/1973 | Ersek | |
| 3,720,959 A * | 3/1973 | Hahn | A61F 2/2846 623/17.17 |
| 5,676,697 A | 10/1997 | McDonald | |
| 5,676,699 A | 10/1997 | Gogolewski et al. | |
| 8,092,513 B2 | 1/2012 | Khosravi et al. | |
| 9,925,046 B2 | 3/2018 | Larsen et al. | |
| 10,258,472 B2 | 4/2019 | Larsen et al. | |
| 10,292,822 B2 | 5/2019 | Larsen et al. | |

(Continued)

FOREIGN PATENT DOCUMENTS

| | | |
|---|---|---|
| CN | 1283090 | 2/2001 |
| CN | 1985780 | 6/2007 |

(Continued)

*Primary Examiner* — Javier G Blanco
(74) *Attorney, Agent, or Firm* — Fay Kaplun & Marcin, LLP (57) ABSTRACT

A graft cage includes cross-sectional portions and longitudinal members. Each portion includes base transverse members forming a cage base; a first arm including first arm transverse members; a second arm including second arm transverse members; base connecting struts, each base connecting strut extending between first one and second one of the base members; first arm connecting struts, each first arm connecting strut extending between a first one of the first members and a second one of the first members; and second arm connecting struts, each second arm connecting strut extending between first one and second one of the second members. The longitudinal members connect the portions to one another. Intersections of the portions with the longitudinal members forming pores in the first and second arms. The pores receive an arm tip of a further graft cage therein to interlock the cage with the further cage.

13 Claims, 12 Drawing Sheets

(56) References Cited

U.S. PATENT DOCUMENTS

| | | |
|---|---|---|
| 10,357,367 B2 | 7/2019 | Daniel et al. |
| 10,507,110 B2 | 12/2019 | Larsen et al. |
| 2001/0018616 A1 | 8/2001 | Schwab |
| 2002/0123750 A1 | 9/2002 | Eisermann et al. |
| 2003/0083746 A1 | 5/2003 | Kuslich |
| 2004/0049270 A1 | 3/2004 | Gewirtz |
| 2005/0015154 A1 | 1/2005 | Lindsey et al. |
| 2005/0192675 A1 | 9/2005 | Robinson |
| 2005/0234557 A1 | 10/2005 | Lambrecht et al. |
| 2006/0282168 A1 | 12/2006 | Sherman et al. |
| 2007/0061015 A1 | 3/2007 | Jensen et al. |
| 2007/0203584 A1 | 8/2007 | Bandyopadhyay et al. |
| 2008/0269745 A1 | 10/2008 | Justin |
| 2010/0310623 A1 | 12/2010 | Laurencin et al. |
| 2011/0054408 A1 | 3/2011 | Wei et al. |
| 2011/0307073 A1 | 12/2011 | Teoh et al. |
| 2012/0029102 A1 | 2/2012 | Rose et al. |
| 2012/0095463 A1 | 4/2012 | Rains et al. |
| 2012/0296441 A1 | 11/2012 | Mikhail et al. |
| 2013/0018482 A1 | 1/2013 | Meridew et al. |
| 2013/0261634 A1 | 10/2013 | McKay |
| 2013/0325129 A1* | 12/2013 | Huang ............... A61F 2/44 623/17.16 |
| 2014/0364961 A1 | 12/2014 | Mikhail et al. |
| 2017/0216033 A1* | 8/2017 | Daniel ............... A61F 2/2846 |
| 2017/0216034 A1 | 8/2017 | Daniel et al. |
| 2017/0231767 A1* | 8/2017 | Larsen ............... A61F 2/2846 623/23.58 |
| 2017/0354503 A1* | 12/2017 | Larsen ............... A61F 2/4601 |
| 2018/0116802 A1 | 5/2018 | Daniel et al. |
| 2018/0193530 A1 | 7/2018 | Barbas et al. |
| 2018/0221152 A1 | 8/2018 | Daniel et al. |
| 2018/0221153 A1 | 8/2018 | Daniel et al. |
| 2019/0076252 A1 | 3/2019 | Karg et al. |
| 2019/0076253 A1 | 3/2019 | Daniel et al. |
| 2019/0151114 A1* | 5/2019 | Sack ............... A61F 2/4455 |
| 2019/0159908 A1 | 5/2019 | Biedermann et al. |
| 2019/0290436 A1 | 9/2019 | Daniel et al. |

FOREIGN PATENT DOCUMENTS

| | | |
|---|---|---|
| CN | 201624812 | 11/2010 |
| CN | 103298429 | 11/2015 |
| CN | 104382636 | 2/2017 |
| CN | 107530169 | 1/2018 |
| CN | 110721010 | 1/2020 |
| EP | 551611 | 7/1993 |
| EP | 1800627 | 6/2017 |
| KR | 20140005174 | 1/2014 |
| WO | 98/38918 | 9/1998 |
| WO | 02/064059 | 8/2002 |
| WO | 2009/025884 | 2/2009 |
| WO | 2010/011941 | 1/2010 |
| WO | 2010/044758 | 4/2010 |
| WO | 2010/093950 | 8/2010 |
| WO | 2011/094748 | 8/2011 |
| WO | 2012/068062 | 5/2012 |
| WO | 2013/006778 | 1/2013 |
| WO | 2018/198138 | 11/2018 |
| WO | WO-2019104392 A1 * | 6/2019 |
| WO | 2020/023936 | 1/2020 |

* cited by examiner

MODULAR BONE GRAFT CAGE

FIELD

The present disclosure relates to a bone graft cage or scaffold. In particular, the present disclosure relates to a modular bone graft cage which may be usable as a stand-alone component or as an assembly with a predetermined configuration.

BACKGROUND

Large bone defects are often treated with implants and/or bone grafts to assist with healing. The bone grafts may be placed in the target area using any of a variety of methods. Prefabricated 2D sheets are often formed to shape by hand, which can be time consuming in the operation room, and can lead to poor results if the shape is not constructed well. Patient-specific implants are typically expensive, require long turnaround times, and often high investment costs for specialized software or software development.

SUMMARY

The present disclosure relates to a graft cage comprising a plurality of cross-sectional portions, each of the cross-sectional portions including (a) a plurality of base transverse members forming a base of the graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions to one another, intersections of the cross-sectional portions with the longitudinal members forming pores in the first and second arms, the pores being sized and shaped to receive an arm tip of a further graft cage therein to interlock the graft cage with the further graft cage.

The present disclosure further relates to a graft cage assembly comprising a first graft cage including a plurality of first graft cage cross-sectional portions, each of the first graft cage cross-sectional portions including (a) a plurality of base transverse members forming a base of the first graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions of the first graft cage to one another, intersections of the cross-sectional portions with the longitudinal members forming pores in the first and second arms and a second graft cage including a plurality of second graft cage cross-sectional portions, each of the second graft cage cross-sectional portions including (a) a plurality of base transverse members forming a base of second the graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions to one another, intersections of the cross-sectional portions with the longitudinal members forming pores in the first and second arms, wherein at least a first one of the pores of the first graft cage is sized, shaped and configured to receive an end of the first arm of the second graft cage to interlock the first and second graft cages to one another.

The present disclosure is further related to method for forming a graft cage assembly comprising interlocking a first graft cage to a second graft cage, wherein the first graft cage includes a plurality of first graft cage cross-sectional portions, each of the first graft cage cross-sectional portions includes (a) a base including a plurality of base transverse members, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions of the first graft cage to one another, intersections of the cross-sectional portions with the longitudinal members forming pores in the first and second arms and a second graft cage including a plurality of second graft cage cross-sectional portions, each of the second graft cage cross-sectional portions including (a) a base including a plurality of base transverse members, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions to one another, intersections of the cross-sectional portions with the longitudinal members forming pores in the first and second arms, the first and second graft cages are interlocked by inserting an end of the first arm of each of first and second ones of the first graft cage cross-sectional portions, respectively, into a first pore formed between first and second ones of the second graft cage cross-sectional portions and a second pore formed between the second one of the second graft cage cross-sectional portions and a third one of the second graft cage cross-sectional portions and inserting a graft material into a first graft containing space between the first and second graft cages.

BRIEF DESCRIPTION

DETAILED DESCRIPTION

The present disclosure may be further understood with reference to the following description and the appended drawings, wherein like elements are referred to with the same reference numerals. The present disclosure relates to graft containment cages or scaffolds that may be used in standalone configurations or may be assembled to create constructs specific to patient anatomy. A standalone cage generally comprises a three-dimensional mesh including multiple cross-sectional U-shapes aligned sequentially in a row, with interconnecting struts between each of the cross-sections. A single cage may be particularly suited for graft containment in e.g. the mandible, while in other embodiments multiple cages may be assembled in configurations suited for e.g. the femur, the tibia, the humerus, etc.

The cages may be assembled by interlocking various aspects of the cages to form temporary connections therebetween that may be further secured via e.g. suturing. Various shapes may be made via an operating physician assembling the cages, to be described in further detail below, to provide strength, flexibility, etc. based on a current need. For example, the cages may be "stacked" to provide a containment cage, or cages may be connected to provide tube-like constructs offering axial stability.

The standalone cages may also be altered by an operating physician. For example, certain struts may be cut to provide axial or torsional flexibility for a cage. The arms, i.e. the side portions of the U-shape, may be shortened when desired, or the axial length of the cage may be reduced by cutting entire U-shape cross sectional portions from the cage. The cages may also be cut in various ways to facilitate their assembly, by e.g. cutting a strut to create a nub that may be employed to interlock the cages.

The cages may, for example, be 3D printed using a polymer e.g. polycaprolactone to provide a flexible cage. In some embodiments, multi-material printing may be used, where individual U-shape cross sections are printed in different materials or of varying stiffness to provide graded stiffness scaffolds. Metal materials may also be used.

FIGS. 1-6 show a graft cage 100 comprising a plurality of U-shaped cross-sectional portions 102 defining a graft containment area 150 therewithin. Each cross-sectional portion 102, e.g. a first cross-sectional portion 102a, a second cross-sectional portion 102b, an Nth cross-sectional portion 102N, comprises a base 104 and two arms 106 extending orthogonally therefrom, the cross-sectional portions 102 being connected to one another via longitudinal members 146 and/or longitudinal struts 108, to be described in further detail below. The arms 106 are described herein as being on a first side of the cage 100, e.g., a first arm 106x and a second side of the cage 100 (i.e., second arm 106y). The parenthetical x or y may be used for other arm components when referring to a particular side of the cage 100 (i.e., a first side comprising the first arm 106x and a second side comprising the second arm 106y), while no parenthetical may be used when referring to either one or both arms.

Any number of cross-sectional portions 102 may be used for a given graft cage. For example, the graft cage 100 shown in FIG. 1 includes fifteen cross-sectional portions 102. However, greater or fewer numbers of cross-sectional portions 102 may be used. For example, a graft cage may be fabricated having any number of cross-sectional portions 102, or a fabricated graft cage may have particular cross-sectional portions 102 cut off by an operating physician depending on a current need. The number of cross-sectional portions 102 may be varied to achieve a desired axial length of the cage 100 and/or the number of cross-sectional portions 102 may be varied in cages 100 of the same length by changing an axial spacing of the cages 100 from one another, as would be understood by those skilled in the art.

Figure 1:
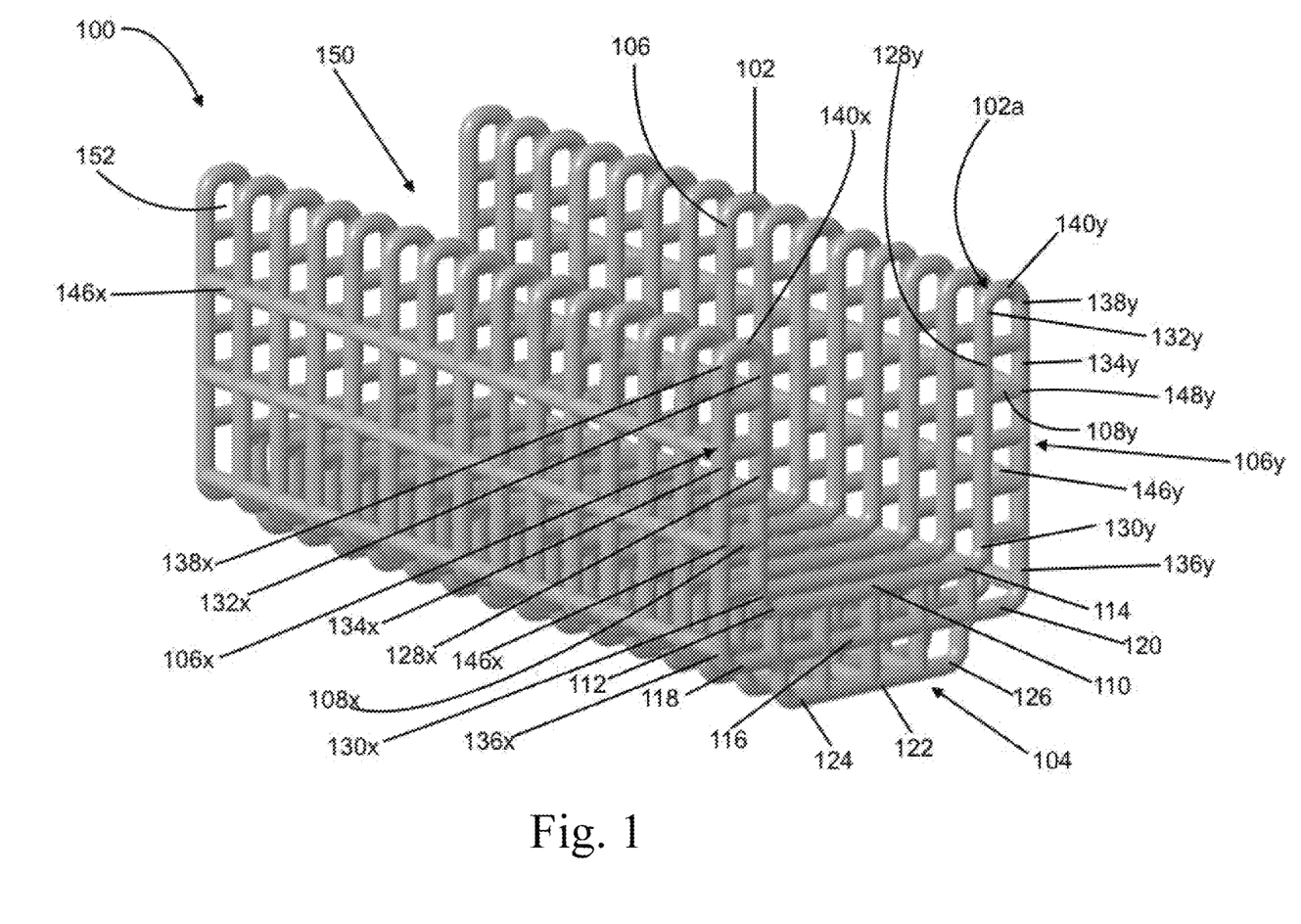
FIG. 1 shows a graft cage comprising a plurality of U-shaped cross-sectional portions defining a graft containment area therewithin.

The base 104 of the cross-sectional portion 102 includes a plurality of transverse members, i.e. an inner transverse member 110 adjacent to the graft containment area, an outer transverse member 122 and a middle transverse member 116 therebetween. The base transverse members 110, 116, 122 of this embodiment are joined to one another via a plurality of struts 108, to be described in further detail below. Each of the arms 106 includes an inner transverse member 128 adjacent to the graft containment area 150 and an outer transverse member 134 joined to one another via a plurality of struts 108. The inner transverse member 110 of the base 104 extends from a first end 112 to a second end 114, the first end 112 joining to the inner transverse member 128x of the first arm 106x and the second end 114 joining to the inner transverse member 128y of the second arm 106y via formed bends. The inner transverse members 128 of the arms 106 extend from a first end 130, joined via the bend to the inner transverse member 110 of the base 104, to a second end 132 at the tips of the U-shape cross-sectional portion 102. Together, the inner transverse members 110, 128x, 128y form a three-sided boundary for the graft containment area 150.

The middle transverse member 116 of the base 104 extends from a first end 118 to a second end 120, the first end 118 joining to the outer transverse member 134x of the first arm 106x and the second end 120 joining to the outer transverse member 134y of the second arm 106y via formed bends, similar to the bend configurations described above. The middle transverse member 116 of this embodiment is longer than the inner transverse member 110, so that outer transverse members 134 of the arms 106 are positioned further outward than the inner transverse members 128 relative to a longitudinal axis of the graft cage 100, to be described further below. The outer transverse members 134 of the arms 106 extend from a first end 136, joined via the bend to the middle transverse member 116 of the base 104, to a second end 138 at the tips of the U-shape cross-sectional portion 102. The second ends 132, 138 of the transverse members 128, 134 of the arm 106 are joined at a tip 140. The outer transverse member 122 of the base 104 extends from a first end 124 to a second end 126 and bends at each end 124, 126 into a connection with the middle transverse member 116 via struts 108.

The transverse members 110, 116, 122 of the base 104 are joined to one another via a plurality of struts 108. In the present embodiment shown in FIG. 1, the inner transverse member 110 and the middle transverse member 116 are connected using five struts 108, and the middle transverse member 116 and the outer transverse member 122 are similarly connected using five struts 108. The transverse members 128, 134 of the arms 106 are connected to one another using four struts 108 (not including the arm tip 140, i.e. the rounded connection at the second ends 132, 138 of the transverse members 128, 134).

However, as would be understood by those skilled in the art, a greater or fewer numbers of struts 108 may be used to make a more or less flexible graft cage 100, or to optimize graft retention properties of the cage 100 while allowing for adequate tissue ingrowth during bone regeneration. It is noted that the graft cage 100 of this embodiment is described as formed with particular members and connecting struts 108. For example, a linear portion of the graft cage 100 spanning a length of greater than one strut offset may be considered a member, with a shorter connection being considered a strut. However, it should be understood that the members/struts may be formed as a unified lattice-like pattern, where the described members/struts do not comprise separate components. Some of the connections may be considered struts even when at least one other "strut" is co-linear relative thereto, e.g. the struts 108 connecting the transverse members 110, 116 and 122 of the base 104.

Figure 2:
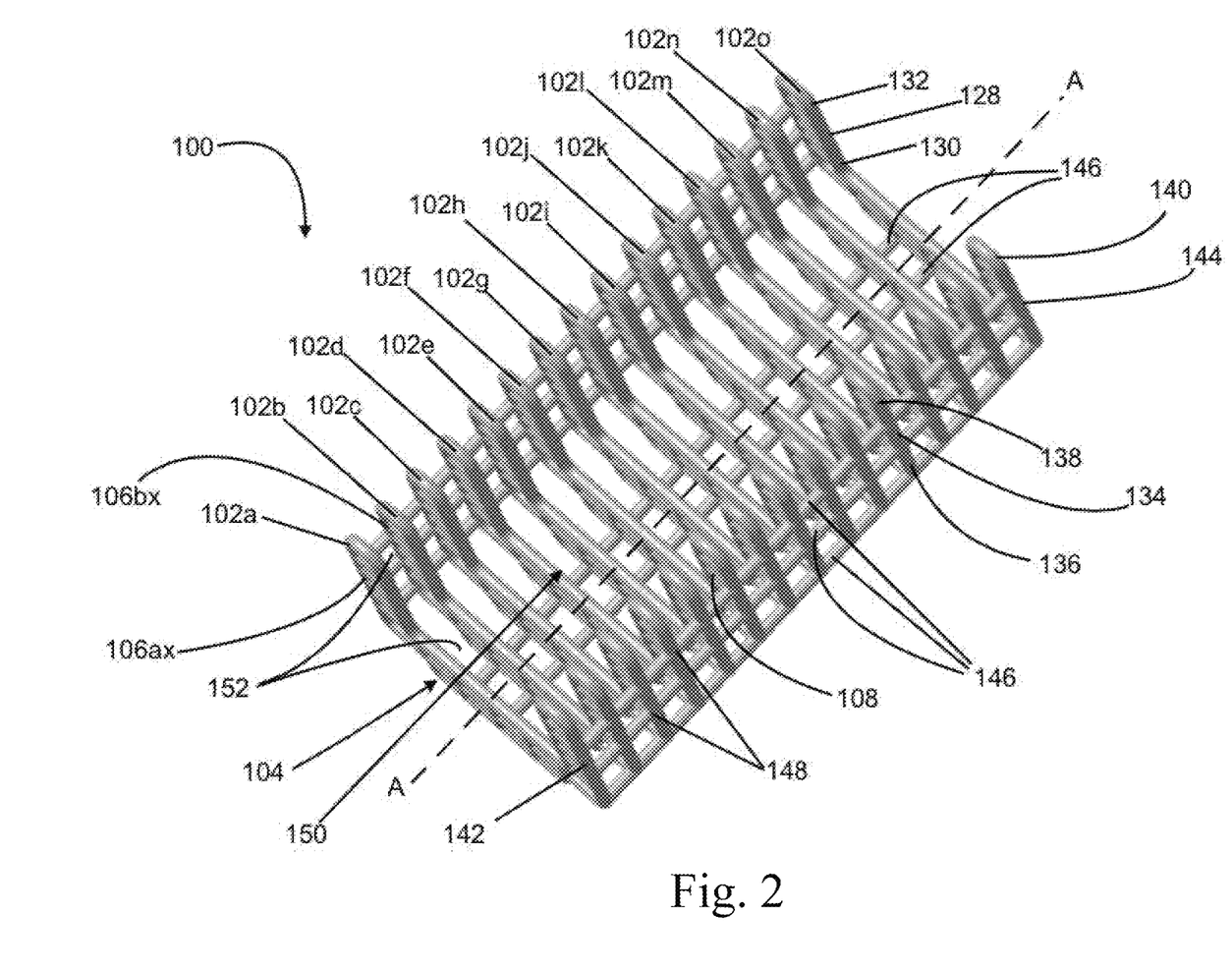
FIG. 2 shows a perspective view of the graft cage of FIG. 1.
Figure 3:
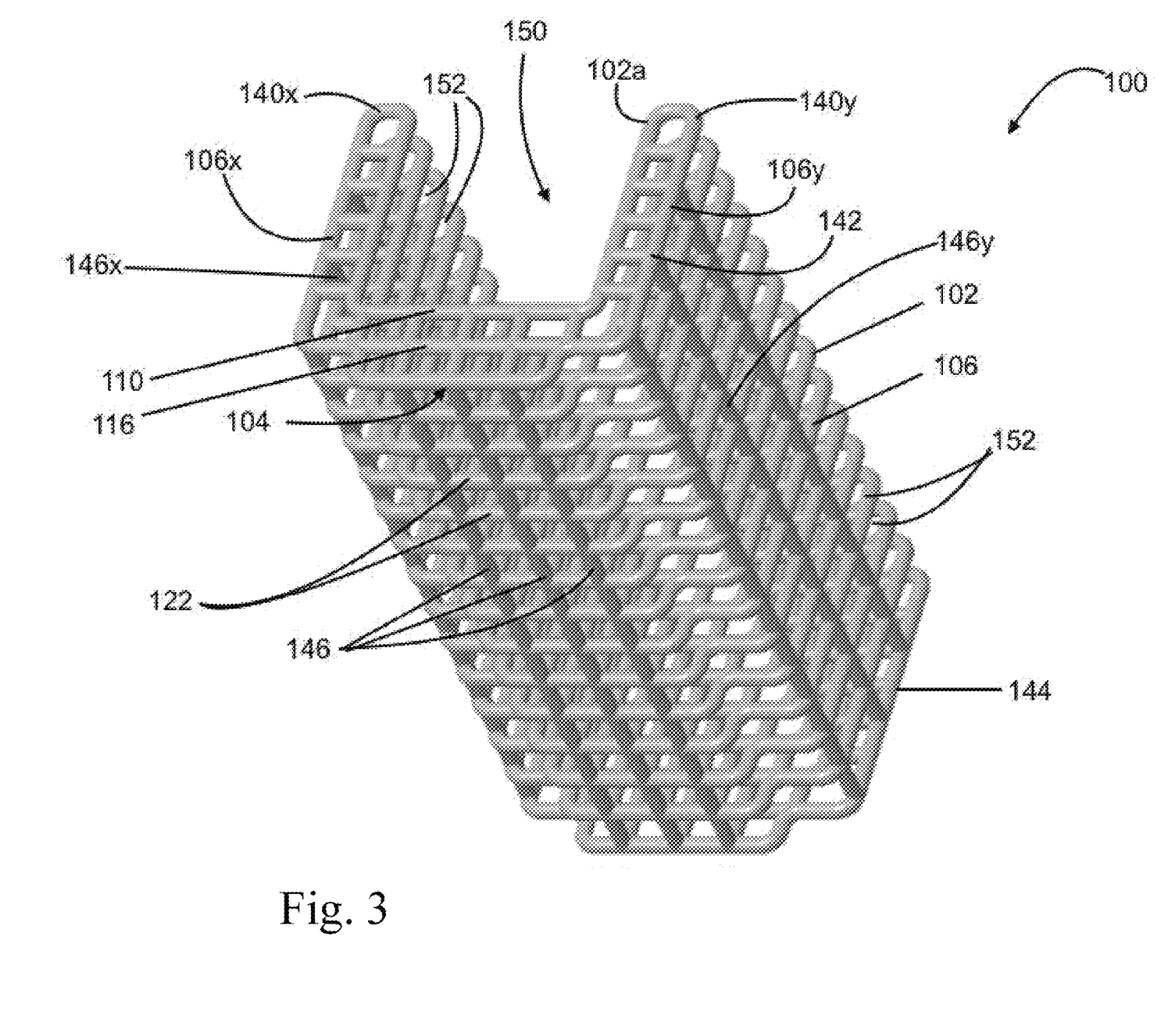
FIG. 3 shows a perspective bottom view of the graft cage of FIG. 1.
Figure 4:
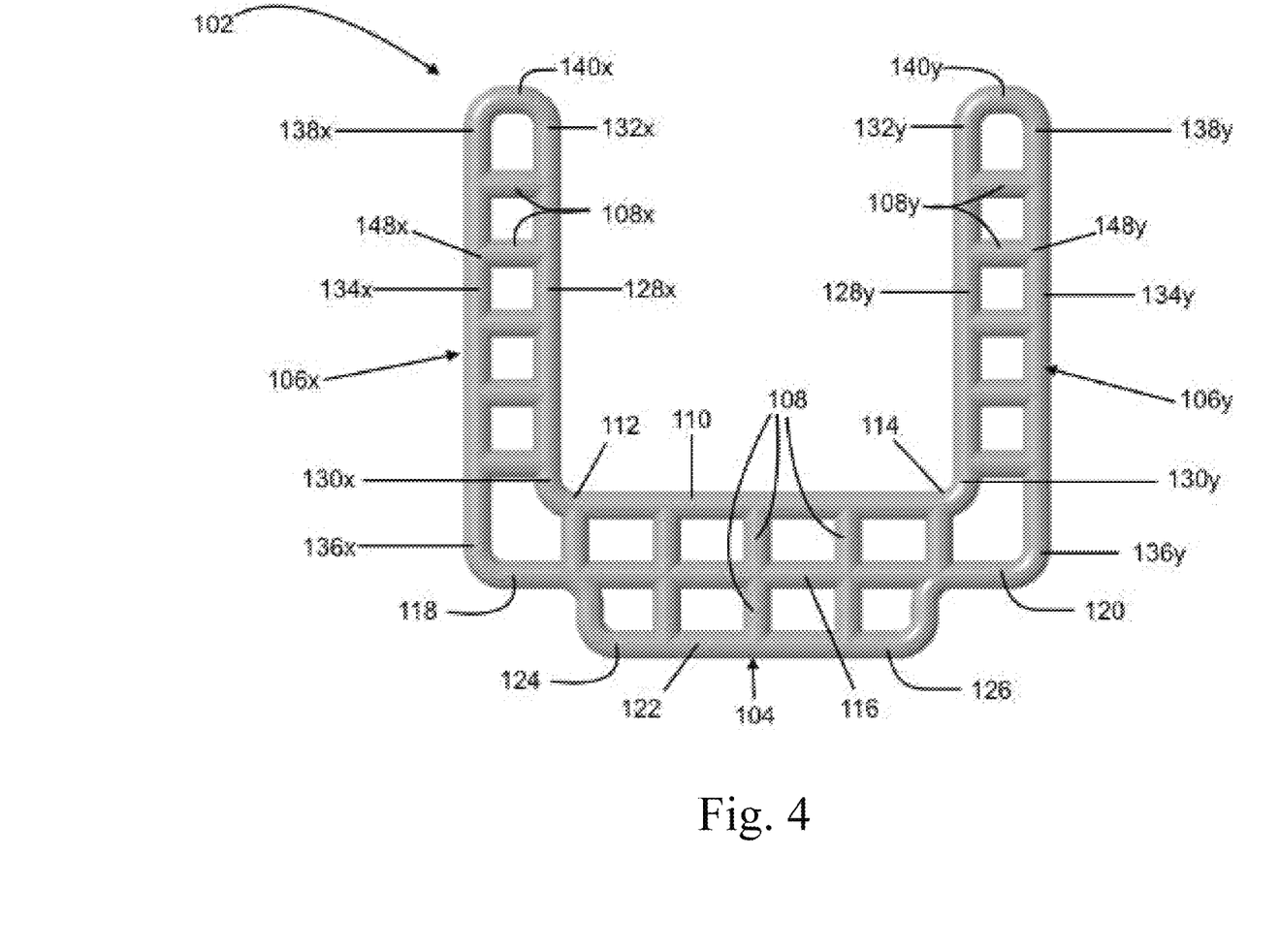
FIG. 4 shows a front view of the graft cage of FIG. 1.
Figure 5:
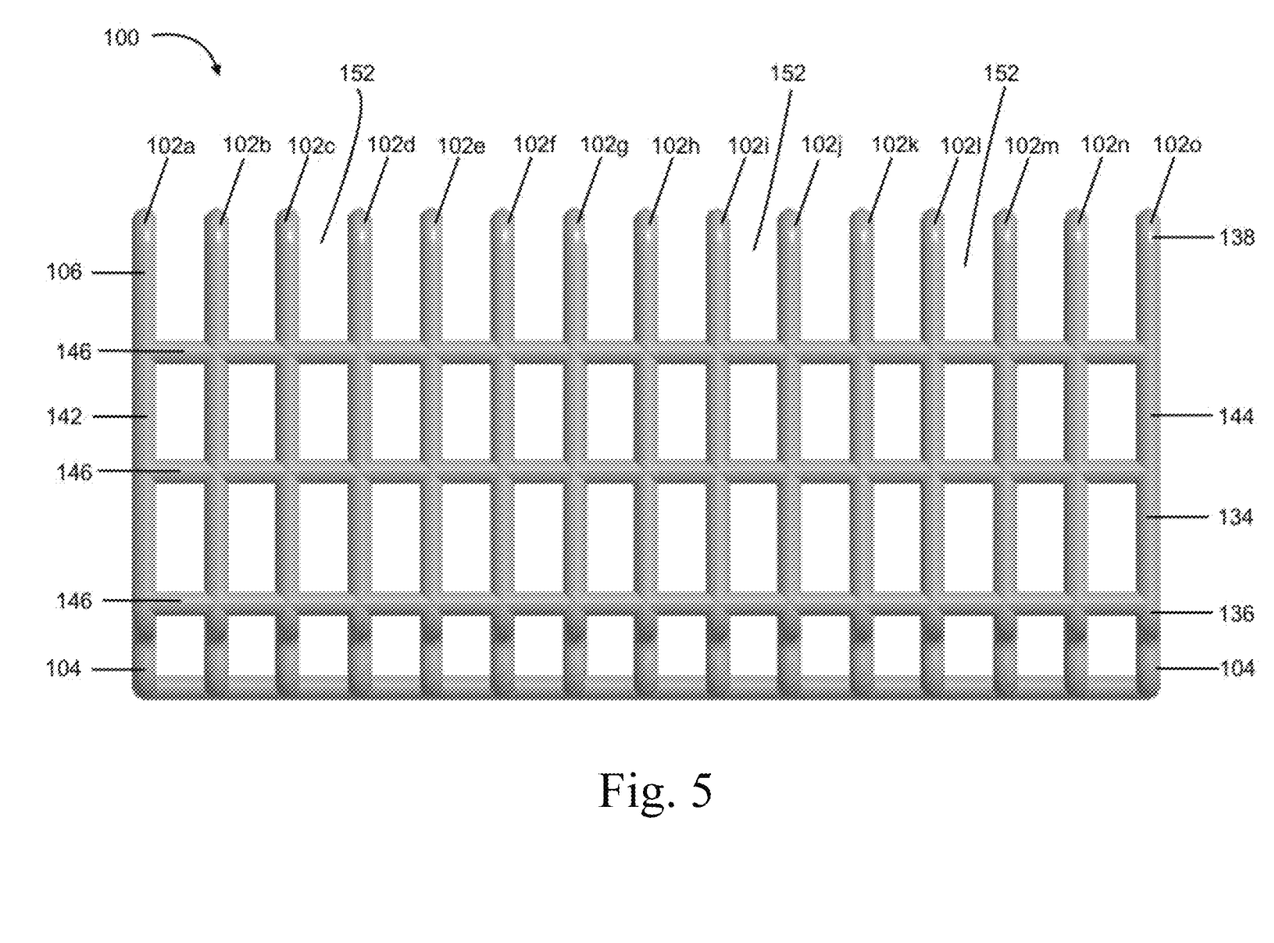
FIG. 5 shows a side view of the graft cage of FIG. 1.
Figure 6:
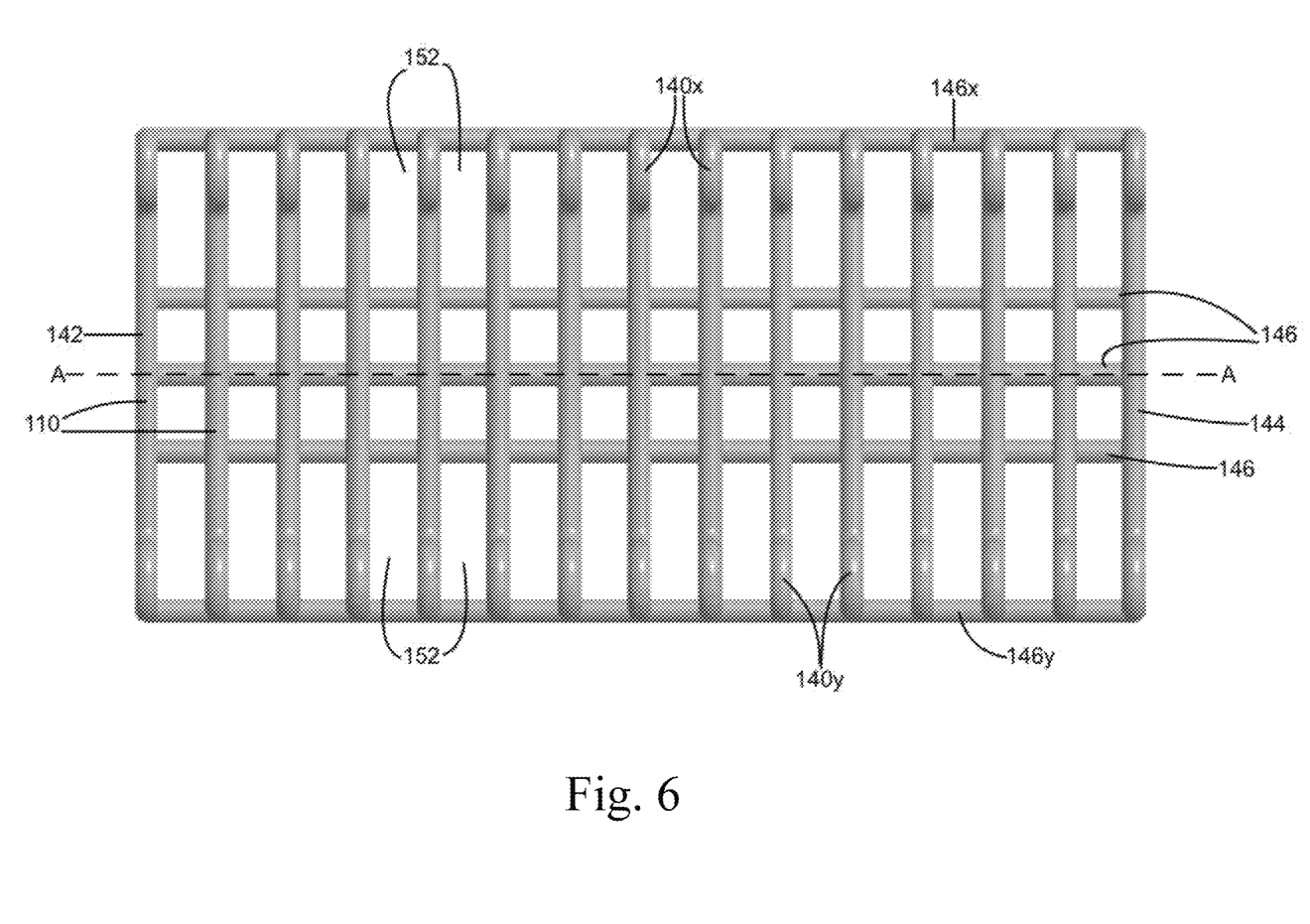
FIG. 6 shows a top view of the graft cage of FIG. 1.

The cross-sectional portion 102 described above may describe each cross-sectional portion 102a, 102b, etc. in a graft cage 100 comprising a plurality of cross-sectional portions 102. As described above, the graft cage 100 shown in FIG. 1 comprises fifteen cross-sectional portions 102a-o spanning from a first end 142 of the cage 100 to a second end 144 of the cage 100 along a longitudinal axis A extending through a center of the graft containment area 150, as shown in FIG. 2. The cross-sectional portions 102 are connected to one another via longitudinal members 146.

Each longitudinal member 146 extends from the first end 142 to the second end 144 of the cage 100 and may intersect with a point 148 at which a transverse member and a transverse strut 108 intersect. For example, each of the points 148 where the outer transverse member 122 of the base 104 intersects with a strut 108 (excluding the ends 124, 126 of the outer transverse member 122) has a longitudinal member 146 extending therefrom along the length of the graft cage 100, connecting the same relative point amongst each of the cross-sectional portions 102. Different numbers of longitudinal members 146 may be used, i.e. not every member/strut intersection point may include a longitudinal member 146 extending therefrom.

For example, considering the arms 106, longitudinal members 146 extend only through two of the member/strut intersection points 148 of a given arm 106, specifically, only at the intersection points 148 at the outer transverse member 134 and additionally at the bend connecting the outer transverse member 134 to the middle transverse member 116 of the base 104. Notably, the tips 140 of the arms 106 do not include longitudinal connecting members 146, in part so that the tips 140 of arms 106 from a first cage 100 may be received in pores 152 of a second cage 200 to facilitate connections therebetween to provide and/or form different graft containment assemblies, to be explained in further below.

In this embodiment, the inner transverse member 128 of the arms 106, the inner transverse member 110 of the base 104 and the middle transverse member 116 of the base 104 do not include any longitudinal members 146 extending therefrom in part so that the flexibility of the graft cage 100 is increased relative to a configuration using more longitudinal members 146. However, in other embodiments, greater or fewer longitudinal members 146 may be used. Additionally, the longitudinal members 146 may connect any respective points in the lattice structures of the cross-sectional portions 102 and need not extend through the intersection points 148 of the members/struts.

The cross-sectional portions 102 may be separated longitudinally relative to one another by a distance selected to facilitate tissue ingrowth for bone regeneration while reducing a cross-sectional area of spaces between the cross-sectional portions 102 to a desired size (e.g., small enough to retain bone graft material therein). For example, the distance between one or more cross-sectional portions 102, e.g., cross-sectional portions 102a and 102b, may be approximately 300 μm or more. Different separation distances may be used depending on the particular application for the graft cage 100, e.g., treating a mandible as compared with treating a tibia. For example, a larger size cage 100 or combination of cages 100 may be used to treat a larger bone and the separation distance between adjacent U-shape cross-sectional portions 102 may be correspondingly larger. Alternatively, the separation distances may vary within a cage if, for example, a particular portion of the cage is likely to have different requirements with regard to the retention of graft material therein.

Cages may be fabricated having differently sized cross-sectional portions, e.g. a cross-sectional portion 102b being larger or smaller than a cross-sectional portion 102a. Cross-sectional portions may also have different separation distances therebetween. Various modifications to the above-described cage may be made. For example, the bends connecting the transverse members of the base with the transverse members of the arms may have a greater or lesser curvature. In another embodiment, the arms may be longer or shorter and/or wider or thinner. The arms may extend from the base at a different angle than shown in the cage 100, e.g., at an oblique angle, or the base may have a curvature, to better fit particular anatomies. In still another embodiment, the extra layer on the outside of the base, i.e., the outer transverse member 122 of base 104 and connecting struts 108, may be removed to achieve greater flexibility. In this embodiment, the cage may more easily fit longer bones.

The various intersecting aspects of the graft cage 100 described above delineate a plurality of pores 152 in the cage 100. A pore 152 may be described by three or four members/struts intersecting to form a two-dimensional area therebetween. A three-dimensional space described by greater numbers of members/struts may also be considered a pore 152, for example, the space defined between the inner and outer transverse members 128, 134 of two adjacent arms 106, e.g., arm 106(a)x and arm 106(b)x, two longitudinal members 146 intersecting the arm transverse members 128, 134 (in most embodiments, the outer transverse member 134 has longitudinal members 146 extending therethrough), and any adjacent struts 108. The pore size is dependent on the specific configuration of the cage 100 and may range from approximately 0.1-100 mm$^2$.

The cages 100 are configured to be interlocked with other cages 100 into various assemblies to create appropriately sized constructs for particular applications. For example, while a stand-alone cage may be well-suited for the mandible, larger assemblies may be used for different bones such as the femur. Two or more cages 100 may be interlocked in various manners to form temporary connections that may be further secured to one another (e.g., via suturing). In one embodiment, the arms tips of a first cage are configured to permit their insertion into the pores of a second cage to form an interlocked assembly.

Figure 7:
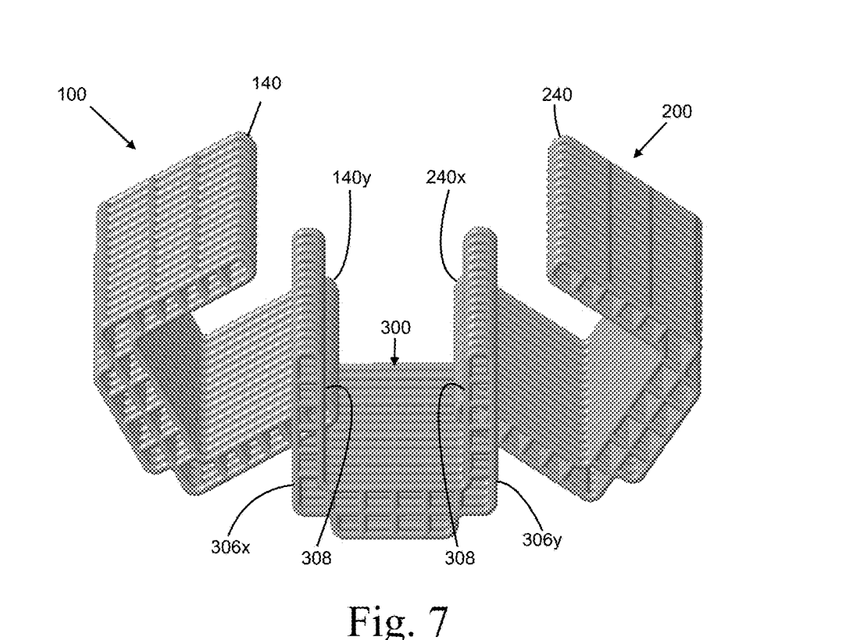
FIG. 7 shows a graft cage assembly according to a first exemplary embodiment.

FIG. 7 shows a graft cage assembly according to a first exemplary embodiment. In this embodiment, arm tips 140, 240 of a first and second cage are inserted into the pores 308 formed in respective arms 306 of a third cage 300. Specifically, the arm tips 140y (on the second side of the first cage 100) are inserted into the pores 308 in the arms 306x (on the first side of the third cage 300) and the arm tips 240x (on the first side of the second cage 200) are inserted into the pores 308 in the arms 306y (on the second side of the third cage). The angle at which the arms are inserted into the pores may vary depending on the respective sizes of the pores and the arms. For example, when an arm is inserted into a pore having a size greater than the width of the arm, the arm may be inserted at an angle within a range.

Figure 8A:
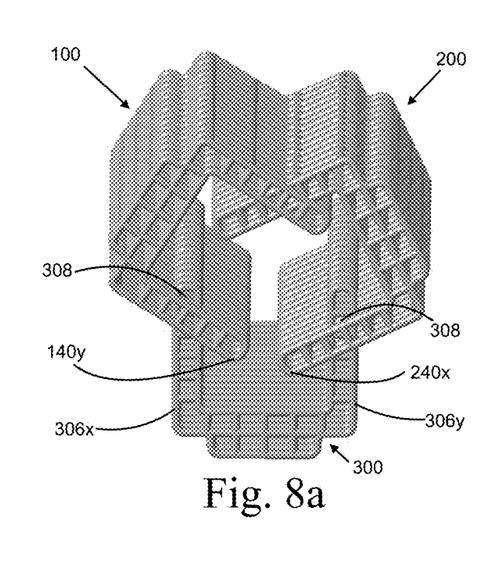
FIGS. 8a-b show a graft cage assembly according to a second exemplary embodiment.
Figure 8B:
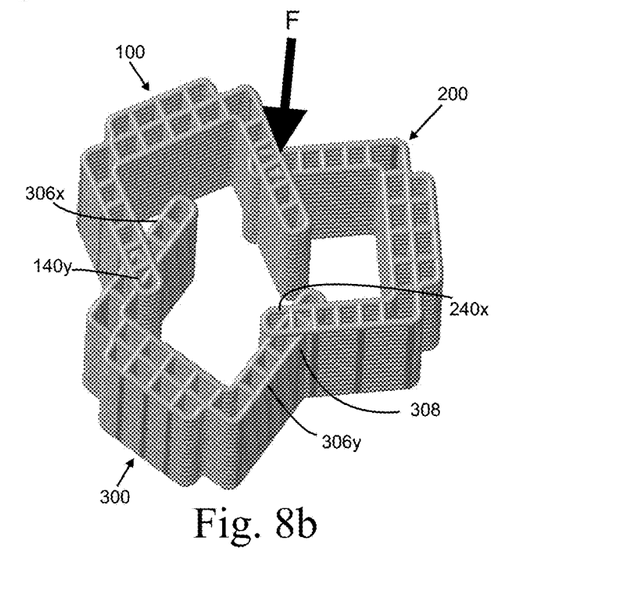

The configuration in FIG. 7 shows the graft cages 100, 200 at respective angles of approximately 60 deg relative to the longitudinal axis of the arms 306x, 306y with which they are connected. However, the angle at which the cages are connected in this embodiment may vary between the angle of ~60 deg shown in FIG. 7 and an angle of ~120 deg. FIGS. 8a-b show a graft cage assembly according to a second exemplary embodiment, where the angle between the first cage 100 and the third cage 300 is ~120 deg, the angle between the second cage 200 and the third cage 300 is ~120 deg, and the first and second cages 100, 200 are additionally interlocked at an angle of ~120 deg, forming a defined tunnel-like structure. The fully circumscribed cross section of the assembly of FIG. 8a has axial stability relative to an "open" assembly, i.e. remains stable even when a longitudinal force F is applied to the assembly, as shown in FIG. 8b. In the embodiments shown in FIGS. 7, 8a and 8b, the first, second and third cages 100, 200, 300 are of a substantially similar size and shape, however this is not required.

Figures 9A, 9B, 9C:
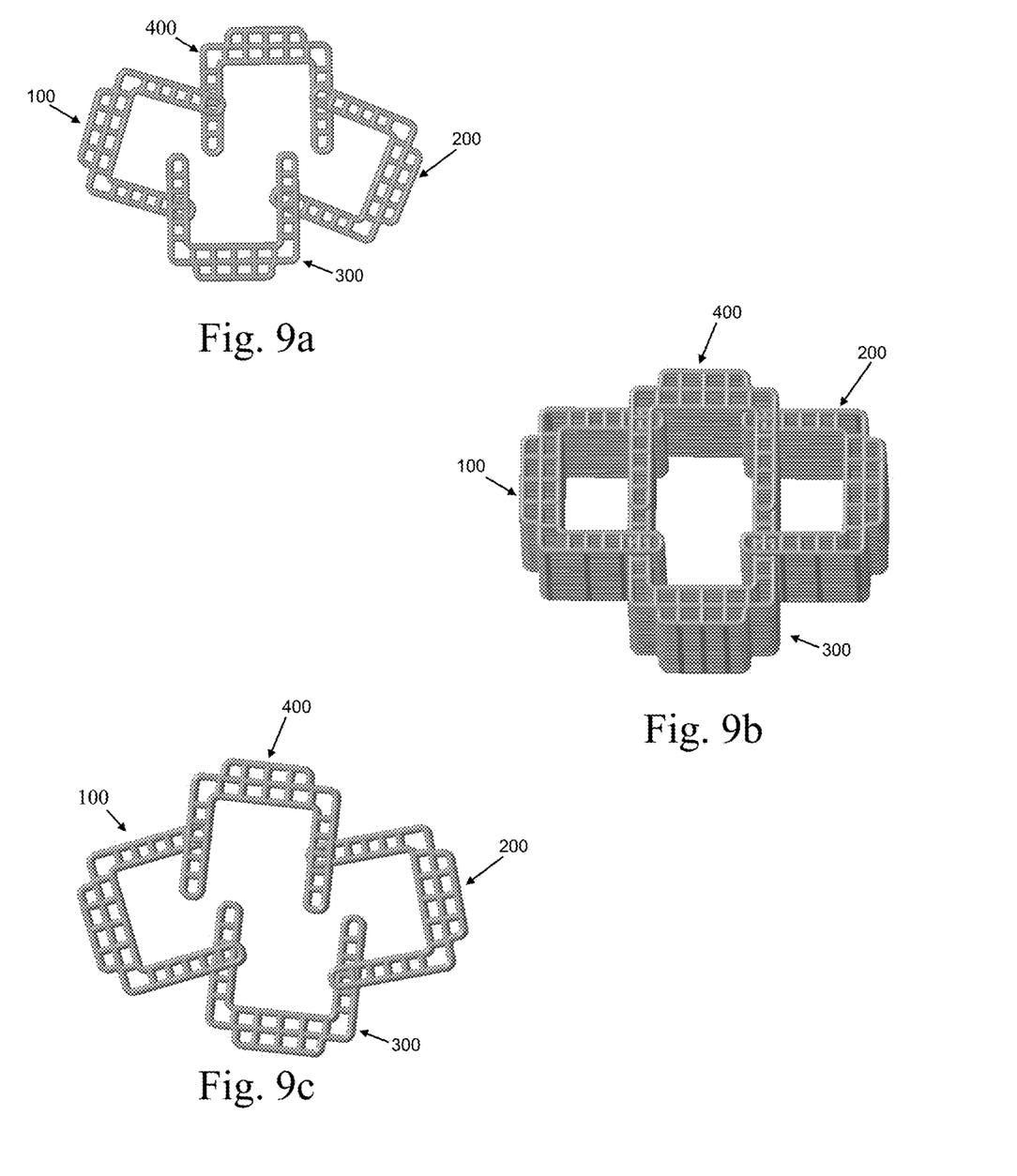
FIG. 9a shows a top view of a graft cage assembly according to a third exemplary embodiment skewed at a first angle.
FIG. 9b shows a perspective view of the graft cage assembly of FIG. 9a in an orthogonal configuration.
FIG. 9c shows a top view of the graft cage assembly of FIG. 9a skewed at a second angle.

FIGS. 9a-c shows a graft cage assembly according to a third exemplary embodiment. In this embodiment, four cages 100, 200, 300, 400 are interlocked in a manner similar to that shown in FIGS. 7-8, i.e. having arm tips interlocking with pores in adjacent arms. However, the hinge-like interlocking allows for a dynamic scaffold that may be intraoperatively adjusted according to a current need. FIG. 9a shows the assembly skewed at a first angle, FIG. 9b shows the assembly in a substantially orthogonal configuration, and FIG. 9c shows the assembly skewed at a second angle opposite the first angle. The pore size relative to the arm width of the interlocking components allows for the dynamic configuration.

Figure 10A:
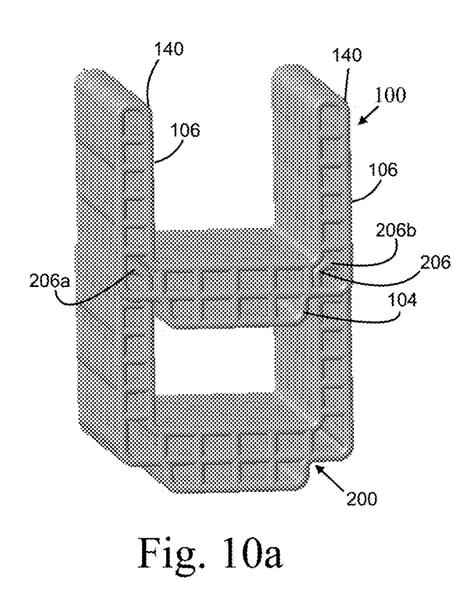
FIGS. 10a-b show a graft cage assembly according to a fourth exemplary embodiment.
Figure 10B:
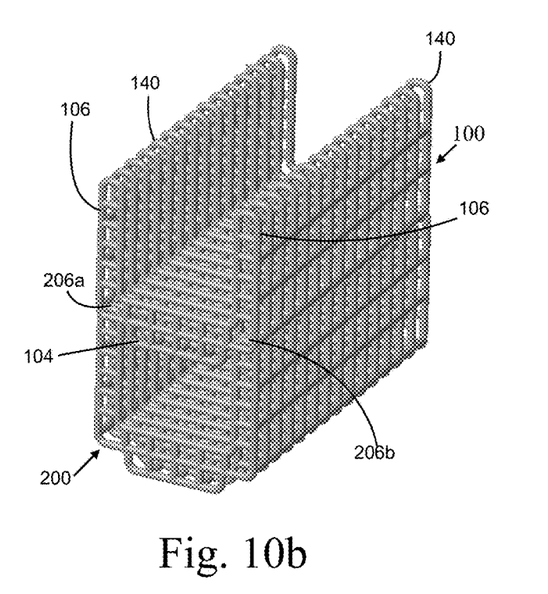

FIGS. 10a-b show a graft cage assembly according to a fourth exemplary embodiment. In this embodiment, two cages 100, 200 are stacked to form a horizontal crib-style containment cage. Cages may be layered on top of one another to reach a necessary height. In this embodiment, the interlock is formed between the bases of the arms 106 of the first cage 100, i.e. the portion of the arms 106 adjacent to the base 104 and opposite the arm tips 140, and the "pores" formed between adjacent arm tips 206, i.e., the space between arm tip 206a and 206b, of the second cage 200. The adjacent arm tips 206 may flex laterally to permit insertion of the bases of the arms 106 into the pores therebetween, the adjacent arm tips 206 having a spring-like tension to retain positional stability of the bases of the arms 106 therein. For example, the crib-style containment cage may be suited for the mandible.

Figure 11:
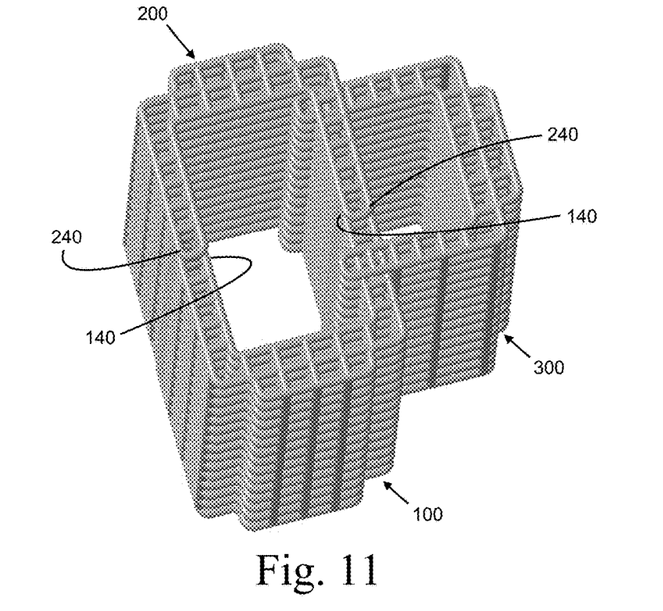
FIG. 11 shows a graft cage assembly according to a fifth exemplary embodiment.

FIG. 11 shows a graft cage assembly according to a fifth exemplary embodiment. In this embodiment, three cages 100, 200, 300 are assembled to create tube-like constructs having axial stability. In this embodiment, the first and second cages 100, 200 are orthogonal to the third cage 300 and positioned opposite one another so that their respective arms tips 140, 240 interlock with one another. This scaffold assembly may be particularly suited for long bones, e.g. the femur or tibia.

The assemblies described above are for illustrative purposes only and the exemplary embodiments are not limited thereto. Many other assemblies are possible using differently sized cages or modified cages. As mentioned above, the standalone cage 100 may be cut in various manners depending on the application. A small or large portion of a cage 100 that has been cut off from the remainder of the cage 100 in an assembly. In addition, by cutting specific struts, the cage 100 may be afforded greater flexibility in a standalone or assembled configuration.

Figure 12A:
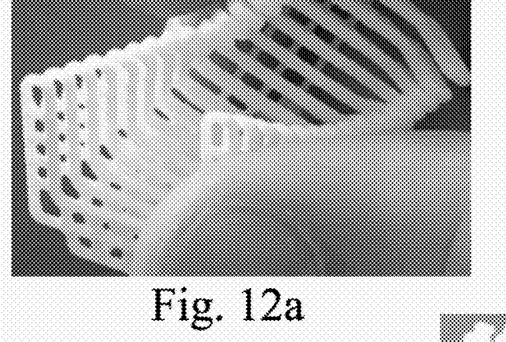
FIGS. 12a-c show a graft cage according to a further exemplary embodiment, where particular struts/members have been cut from the graft cage of FIG. 1 to provide greater torsional and greater axial flexibility.
Figure 12B:
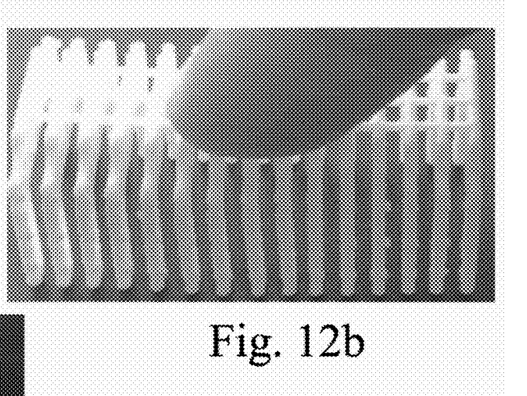
Figure 12C:
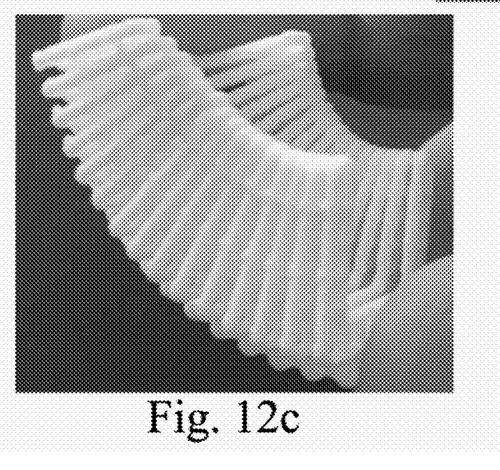

FIGS. 12a-c show a graft cage 800 according to a further exemplary embodiment, where particular struts/members have been cut from the graft cage 100 to increase the torsional flexibility of the cage 800. For example, multiple sections of the longitudinal members 146 of the graft cage 100 have been cut to eliminate the resistance these connections would otherwise have applied to restrict torsional bending of the cage 800. In the example embodiment, all struts/members have been cut except for one layer of longitudinal members 146 connecting the outer transverse members 122 of the graft cage 800 to one another. FIG. 12b shows the graft cage 800 with a lateral force applied thereto, demonstrating that the cage 800 retains lateral stability even after the longitudinal members 146 have been cut. FIG. 12c shows the graft cage 800 having a greater axial flexibility.

Figure 13:
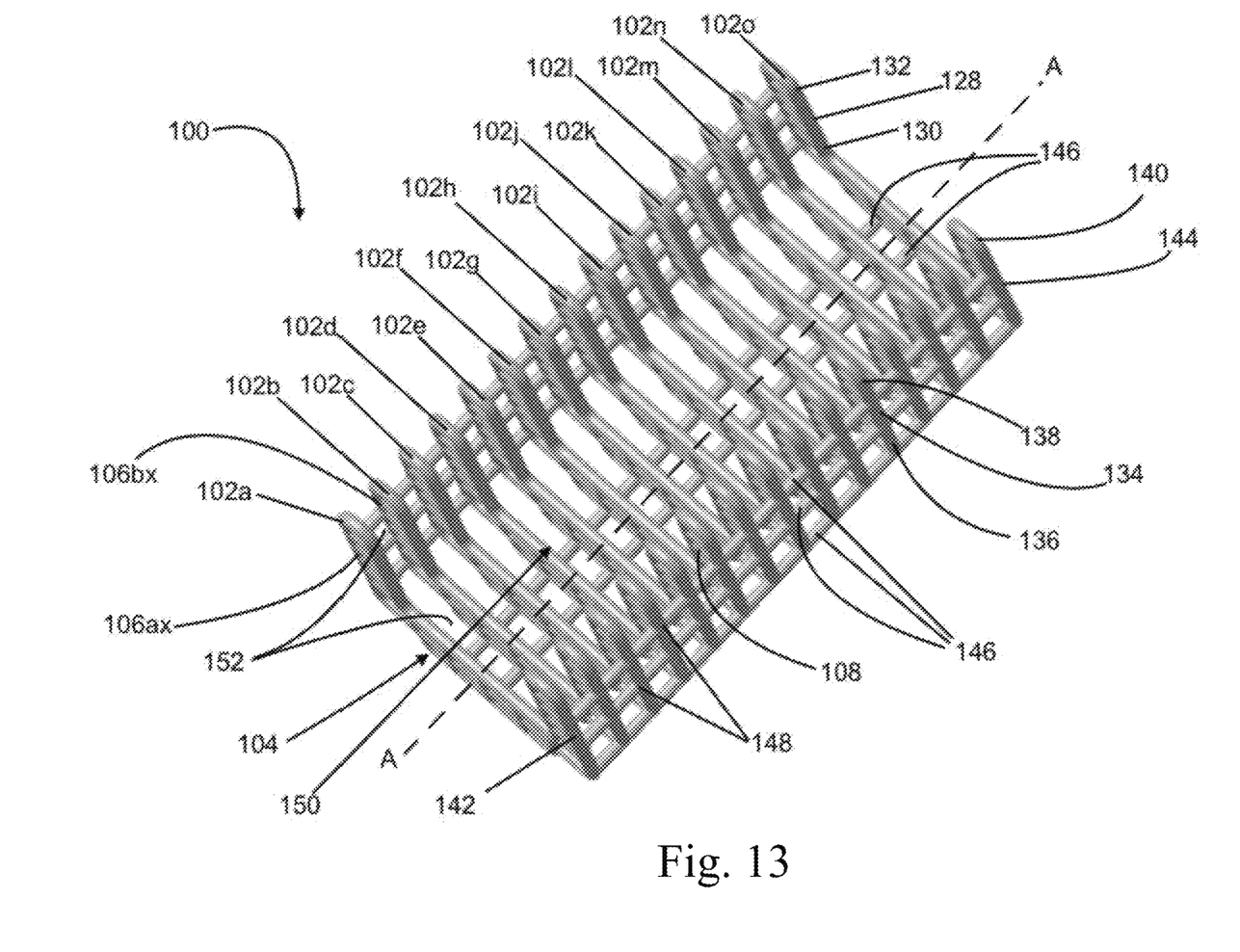
FIG. 13 shows a graft cage according to yet another exemplary embodiment where a separation distance between a first one of the cross-sectional portions and second one of the cross-sectional portions adjacent to the first cross-sectional portion is different than a distance between a third one of the cross-sectional portions and a fourth one of the cross-sectional portions adjacent to the third cross-sectional portion.
Figure 14:
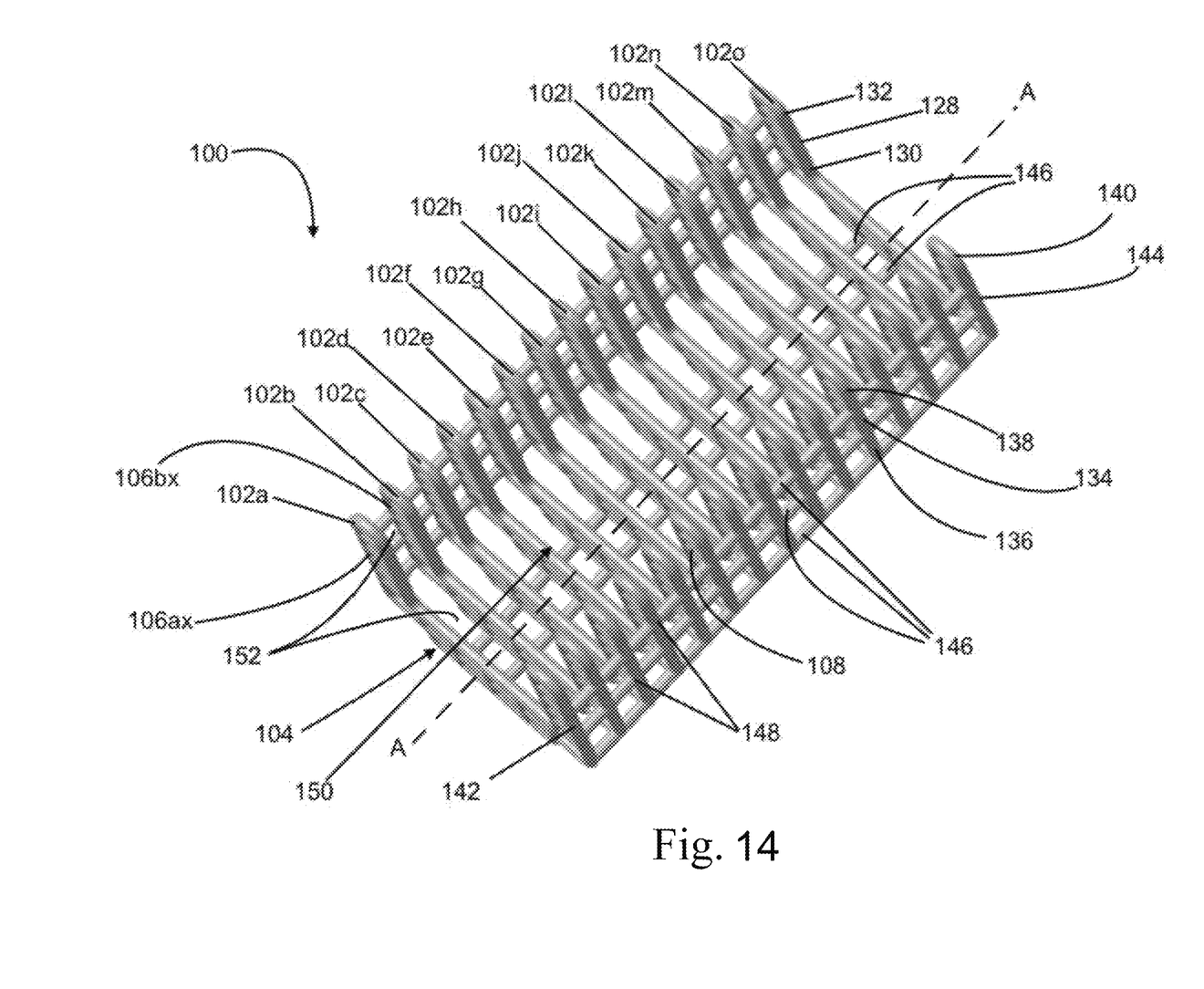
FIG. 14 shows a graft cage according to a further exemplary embodiment where a cross-sectional area of the first cross-sectional portion is larger than a cross-sectional area of the third cross-sectional portion.

FIG. 13 shows a graft cage where a separation distance between a first one of the cross-sectional portions and second one of the cross-sectional portions adjacent to the first cross-sectional portion is different than a distance between a third one of the cross-sectional portions and a fourth one of the cross-sectional portions adjacent to the third cross-sectional portion. FIG. 14 shows a graft cage where a cross-sectional area of the first cross-sectional portion is larger than a cross-sectional area of the third cross-sectional portion.

A graft cage may also be cut to facilitate a better interlock between cages. The nubs left over after cutting the struts may provide a surface that may lodge between the struts of an adjoining cage. Nubs such as those remaining after a cut may also be purposely formed during fabrication of the cage, for example in key locations that are oft-used when assembling multiple cages. These small protuberances provide not only an initial interlocking surface, but a surface for supporting subsequent suturing that further strengthens the connections between the cages.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A graft cage system, comprising:
   a first graft cage including:
      a plurality of first graft cage cross-sectional portions, each of the first graft cage cross-sectional portions including (a) a plurality of base transverse members forming a base of the first graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members; and
      a plurality of longitudinal members connecting the first graft cage cross-sectional portions to one another, intersections of the first graft cage cross-sectional portions with the longitudinal members forming first pores in the first and second arms;
   a second graft cage including:
      a plurality of second graft cage cross-sectional portions, each of the second graft cage cross-sectional portions including (a) a plurality of base transverse members forming a base of the second graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members: and
      a plurality of longitudinal members connecting the second graft cage cross-sectional portions to one another, intersections of the second graft cage cross-sectional portions with the longitudinal members forming second pores in the first and second arms; and
   a third graft cage comprising:
      a plurality of third graft cage cross-sectional portions, each of the third graft cage cross-sectional portions including (a) a plurality of base transverse members forming a base of the third graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members; and
      a plurality of longitudinal members connecting the third graft cage cross-sectional portions to one another, intersections of the third graft cage cross-sectional portions with the longitudinal members forming third pores in the first and second arms, wherein the first, second, and third graft cages are sized, shaped and configured so that a free end of the first arm of the first graft cage may be interlocked with a free end of the second arm of the second graft cage while a the free end of the first arm of the second graft cage is interlocked with a free end of the second arm of the third graft cage and a free end of the first arm of the third graft cage is interlocked with a free end of the second arm of the first graft cage, the first pores being sized and shaped and configured to receive the free end of the second arm of the second graft cage on the first arm of the first graft cage and to receive the free end of the first arm of the third graft cage on the second arm of the first graft cage therein to interlock the first graft cage with the second and third graft cages.

2. The graft cage system of claim 1, further comprising a graft containment area of the first graft cage bounded by the base and the first and second arms of the first graft cage.

3. The graft cage system of claim 1, wherein the first base transverse member of the first graft cage is shorter than the second base transverse member of the first graft cage.

4. The graft cage system of claim 1, wherein at least two of the first graft cage cross-sectional portions are substantially U-shaped.

5. The graft cage system of claim 1, wherein a separation distance between a first one of the first graft cage cross-sectional portions and second one of the first graft cage cross-sectional portions adjacent to the first graft cage cross-sectional portion is different than a distance between a third one of the first graft cage cross-sectional portions and a fourth one of the first graft cage cross-sectional portions adjacent to the third first graft cage cross-sectional portion.

6. The graft cage system of claim 5, wherein a cross-sectional area of the first graft cage cross-sectional portion is larger than a cross-sectional area of the third first graft cage cross-sectional portion.

7. The graft cage system of claim 1, wherein the base of the first graft cage includes a third base transverse member.

8. The graft cage system of claim 1, wherein the first pores are sized and shaped and configured to hold a desired graft material within the first graft cage.

9. The graft cage system of claim 1, wherein the longitudinal members of the first graft cage connect respective bases of the first graft cage cross-sectional portions to one another.

10. A graft cage assembly, comprising:
a first graft cage including a plurality of first graft cage cross-sectional portions, each of the first graft cage cross-sectional portions including (a) a plurality of base transverse members forming a base of the first graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions of the first graft cage to one another, intersections of the cross-sectional portions with the longitudinal members forming pores in the first and second arms; and
a second graft cage including a plurality of second graft cage cross-sectional portions, each of the second graft cage cross-sectional portions including (a) a plurality of base transverse members forming a base of second the graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions of the second graft cage to one another, intersections of the cross-sectional portions with the longitudinal members forming pores in the first and second arms; and
a third graft cage including a plurality of third graft cage cross-sectional portions, each of the third graft cage cross-sectional portions including (a) a plurality of base transverse members forming a base of the third graft cage, (b) a first arm including a plurality of first arm transverse members, (c) a second arm including a plurality of second arm transverse members, (d) a plurality of base connecting struts, each of the base connecting struts extending between a first one of the base transverse members and a second one of the base transverse members, (e) a plurality of first arm connecting struts, each of the first arm connecting struts extending between a first one of the first arm transverse members and a second one of the first arm transverse members, and (f) a plurality of second arm connecting struts, each of the second arm connecting struts extending between a first one of the second arm transverse members and a second one of the second arm transverse members and a plurality of longitudinal members connecting the cross-sectional portions of the third graft cage to one another, intersections of the cross-sectional portions with the longitudinal members forming pores in the first and second arms, each of the first and second arms of the third graft cage extending from a base end adjacent to a base of the third graft cage to a free end opposite the corresponding base end;
wherein at least a first one of the pores of the first graft cage is sized, shaped and configured to receive an end of the first arm of the second graft cage to interlock the first and second graft cages to one another;
wherein the first, second, and third graft cages are sized, shaped and configured so that a free end of the first arm of the first graft cage may be interlocked with a free end of the second arm of the second graft cage while a free end of the first arm of the second graft cage is interlocked with a free end of the second arm of the third graft cage and a free end of the first arm of the third graft cage is interlocked with a free end of the second arm of the first graft cage.

11. The graft cage assembly of claim 10, wherein a first angle of the first graft cage between the base and the first arm of the first graft cage is equal to a second angle of the first graft cage between the base and the second arm of the first graft cage and a first angle of the second graft cage between the base and the first arm of the second graft cage is equal to a second angle of the second graft cage between the base and the second arm of the second graft cage, and wherein the first and second angles of the first graft cage are equal to the first and second angles of the second graft cage.

12. The graft cage assembly of 10, wherein a first connection angle between the first arm of the first graft cage and the second arm of the second graft cage is equal to a second connection angle between the second arm of the first graft cage and the first arm of the third graft cage.

13. The graft cage assembly of claim 12, wherein the first connection angle is between 60 degrees and 120 degrees.

* * * * *